(12) United States Patent
Gilkerson et al.

(10) Patent No.: US 6,304,778 B1
(45) Date of Patent: Oct. 16, 2001

(54) IMPLANTABLE DEFIBRILLATORS WITH PROGRAMMABLE CROSS-CHAMBER BLANKING

(75) Inventors: James O. Gilkerson, Stillwater; Doug M. Birkholz, Shoreview; David L. Perschbacher, Coon Rapids, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/377,803

(22) Filed: Aug. 20, 1999

(51) Int. Cl.⁷ ................................................ A61N 1/39
(52) U.S. Cl. ....................................................... 607/5
(58) Field of Search .................... 607/4, 5, 9, 13, 607/14, 30

(56) References Cited

U.S. PATENT DOCUMENTS

| | | | |
|---|---|---|---|
| 4,825,869 | 5/1989 | Sasmor et al. | 128/419 PT |
| 4,928,674 | 5/1990 | Halperin et al. | 128/30.2 |
| 5,107,833 | 4/1992 | Barsness | 128/419 PT |
| 5,243,976 | 9/1993 | Ferek-Petric et al. | 607/6 |
| 5,311,183 | 5/1994 | Mathews et al. | 342/26 |
| 5,316,001 | 5/1994 | Ferek-Petric et al. | 128/661.08 |
| 5,366,488 * | 11/1994 | Franberg et al. | 607/9 |
| 5,462,060 | 10/1995 | Jacobson et al. | 128/702 |
| 5,476,485 | 12/1995 | Weinberg et al. | 607/28 |
| 5,755,739 | 5/1998 | Sun et al. | 607/14 |
| 5,776,167 | 7/1998 | Levine et al. | 607/9 |
| 5,782,876 | 7/1998 | Flammang | 607/4 |
| 5,871,512 | 2/1999 | Hemming et al. | 607/28 |
| 5,873,898 | 2/1999 | Hemming et al. | 607/28 |
| 6,067,472 | 5/2000 | Vonk et al. | 607/28 |
| 6,112,119 | 8/2000 | Schuelke et al. | 607/9 |

* cited by examiner

*Primary Examiner*—Scott M. Getzon
(74) *Attorney, Agent, or Firm*—Schwegman, Lundberg, Woessner & Kluth, P.A.; Eduardo E. Drake

(57) ABSTRACT

Miniature defibrillators and cardioverters detect abnormal heart rhythms and automatically apply electrical therapy to restore normal heart function. Therapy decisions are typically based on the time between successive beats of various chambers of the heart, such as the left atrium and left ventricle. To prevent confusing a left ventricle beat for a left atrium beat, some devices use cross-chamber blanking, a technique which disables sensing of atrial beats for a certain time period after sensing. Conventionally, these devices lack any mechanism for adjusting length of this period. Accordingly, the inventor devised a implantable device including a mechanism for adjusting this time period. This mechanism ultimately allows tailoring of the cross-chamber blanking period to fit the needs of individual patients.

7 Claims, 2 Drawing Sheets

IMPLANTABLE DEFIBRILLATORS WITH PROGRAMMABLE CROSS-CHAMBER BLANKING

TECHNICAL FIELD

The present invention concerns implantable defibrillators and cardioverters and methods for ensuring accurate interval measurements in these devices.

BACKGROUND OF THE INVENTION

Since the early 1980s, thousands of patients prone to irregular and sometimes life threatening heart rhythms have had miniature defibrillators and cardioverters implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The typical defibrillator or cardioverter includes a set of electrical leads, which extend from a sealed housing through the veinous system into the inner walls of a heart after implantation. Within the housing are a battery for supplying power, a capacitor for delivering bursts of electric current through the leads to the heart, and monitoring circuitry for monitoring the heart and determining not only when and where to apply the current bursts but also their number and magnitude. The monitoring circuitry generally includes a microprocessor and a memory that stores instructions directing the microprocessor to interpret electrical signals that naturally occur in the heart as normal or abnormal rhythms. For abnormal rhythms, the instructions, or more generally signal-processing algorithm, tell the processor what, if any, electrical therapy should be given to restore normal heart function.

In general, these algorithms use the time intervals between successive heart beats, or cardiac events, as key determinants of therapy decisions. Thus, to ensure the validity of therapy decisions, it is very important to ensure accuracy of these intervals.

Determining these intervals can be especially problematic in dual-chamber defibrillation and cardioversion devices, which monitor the beats of two chambers of the heart, such as the left ventricle and the left atrium. In these devices, there is a significant risk of mistaking a ventricle beat for an atrial beat, and therefore counting too many atrial beats and miscalculating some atrial intervals (the time between atrial beats). Because of this risk, many dual-chamber devices use a technique, known as cross-chamber blanking, to ensure accuracy of atrial interval measurements.

Cross-chamber blanking entails using a blanking period to prevent sensing atrial beats for a certain time period after the last ventricular beat. In other words, atrial sensing is temporarily disabled after each ventricular beat to prevent mistaking the ventricular beat for an atrial beat. In conventional dual-chamber devices, the length, or duration, of the blanking period is fixed during manufacture and cannot be tailored to fit the unique needs of some patients. Accordingly, the inventors recognized a need for dual-chamber defibrillation and cardioversion devices that have programmable cross-chamber blanking periods.

SUMMARY OF THE INVENTION

To address this and other needs, the inventor devised a dual-chamber implantable defibrillation and/or cardioversion device which includes a memory storing one or more programmable or reprogrammable settings for use as a cross-chamber blanking period. An exemplary embodiment applies one of the settings to disable atrial sensing for a period of time based on the programmed setting. Ultimately, various embodiments of the invention facilitate tailoring defibrillation and/or cardioversion devices to individual patients.

DESCRIPTION OF THE PREFERRED EMBODIMENTS

Figure 1:
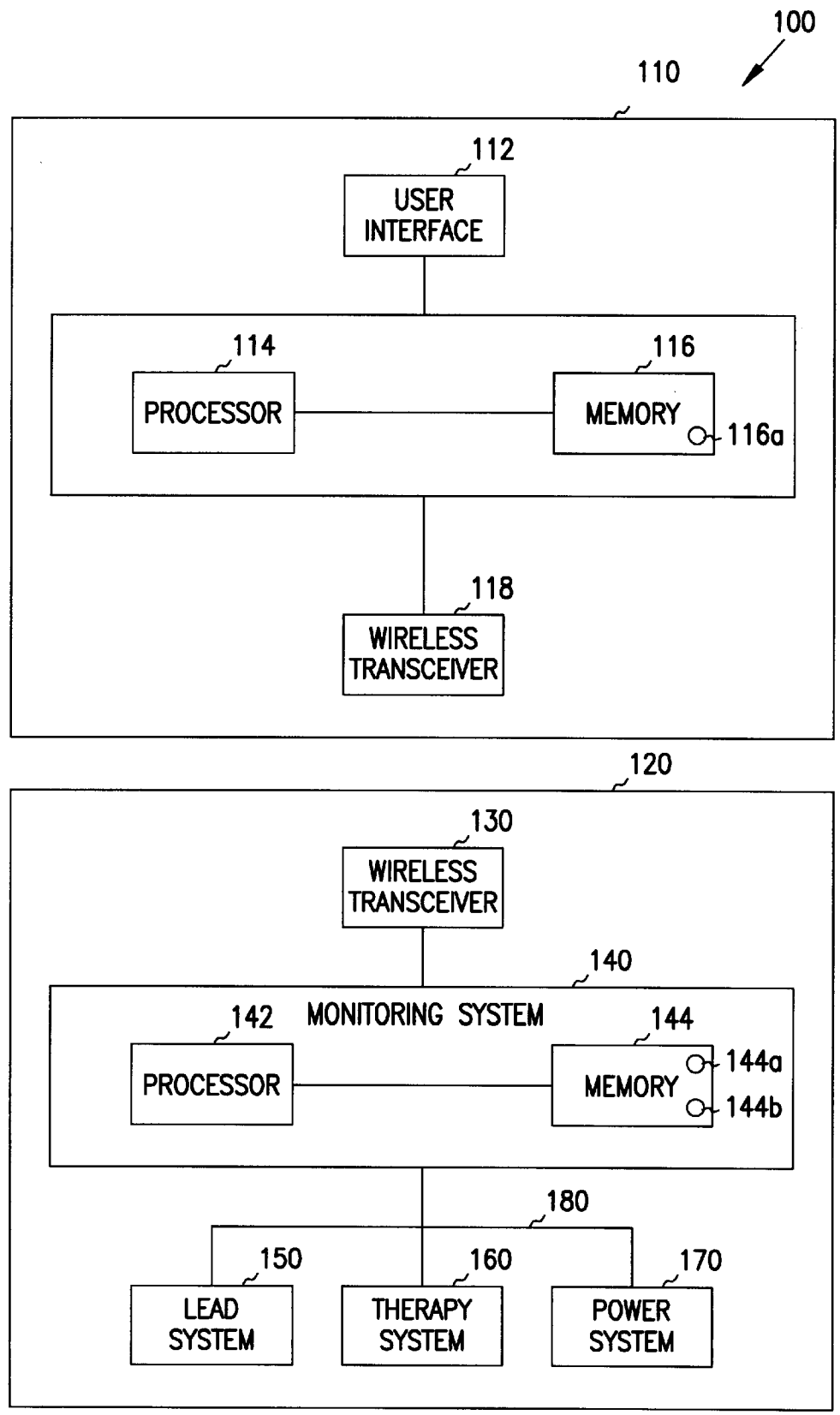
FIG. 1 is a block diagram of an exemplary medical device system 100 incorporating teachings of the present invention.
Figure 2:
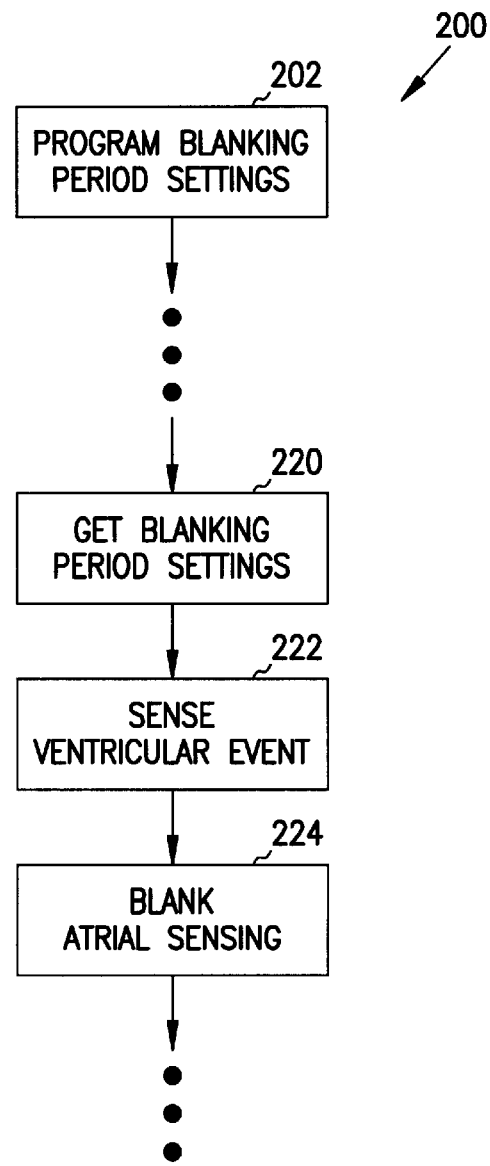
FIG. 2 is a flow chart illustrating an exemplary method incorporating teachings of the present invention.
Figure 3:
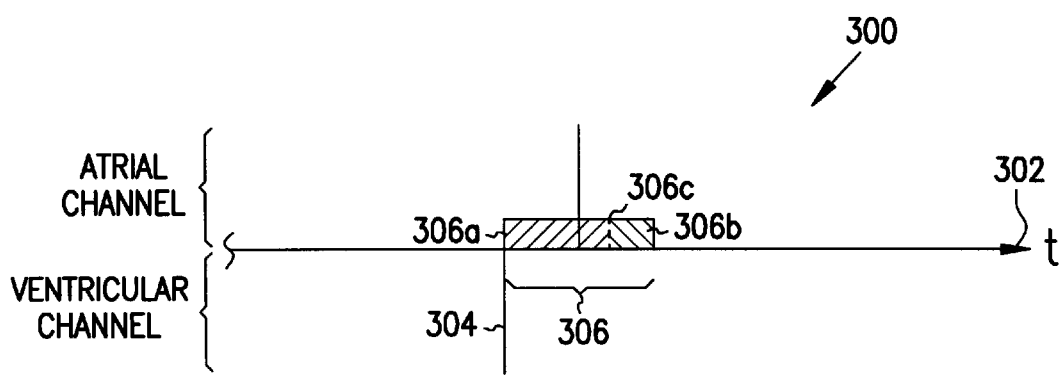
FIG. 3 is an exemplary timing diagram illustrating operation of the present invention.

The following detailed description, which references and incorporates FIGS. 1–3, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

FIG. 1 shows an exemplary medical device system 100 which includes a device programmer 110 and an implantable dual-chamber defibrillation and/or cardioversion device 120 in accord with teachings of the present invention. Device programmer 110, which generally communicates programming information, such as one or more cross-chamber blanking settings, to defibrillator 120, includes a user interface 112, microcontroller or processor 114, a memory 116, and a wireless transceiver 118.

User interface 112, which includes a keyboard and graphical-user interface (not shown) generated by processor 114, facilitates selection of one or more cross-chamber settings or insertion of one or more manual settings, during a refractory programming mode. Memory 116 stores, among other things, a number of cross-chamber blanking settings 116a, for example a set of times ranging from 30–200 milliseconds in 10-millisecond increments or a set of temporal indices which can be used to determine duration of a blanking period. Settings 116a are displayed for user selection by user interface 112 during the programming mode.

In the exemplary embodiment, determination of appropriate blanking period settings or times follows an iterative procedure of visually analyzing electrogram data to determine whether a particular cross-chamber blanking period is either too long or too short, programming a new blanking period, and then visually analyzing updated electrogram data. The selected or manually inserted settings can then be communicated alone or in combination with other programmable parameters into implantable device 120.

Implantable dual-chamber device 120 includes a wireless transceiver 130 monitoring system 140, a lead system 150, a therapy system 160, a power system 170, and an interconnective bus 180. Wireless transceiver 130 communicates with wireless transceiver 118 of device programmer 110. Monitoring system 140 includes a processor or microcontroller 142 and a memory 144. Memory 144 includes one or more software modules 144a which store one or more computer instructions in accord with the present invention. Additionally, memory 144 includes one or more parameter storage portions 144b which store one or more programmed cross-chamber blanking settings in accord with the present invention.

Some embodiments of the invention replace software modules 144a with one or more hardware or firmware modules. In the exemplary embodiment, processor 142 is a ZiLOG™ Z80 microprocessor (with a math coprocessor). However, the invention is not limited to any particular microprocessor, microcontroller, or memory.

Lead system 150, in the exemplary embodiment, includes one or more electrically conductive leads—for example, atrial, ventricular, or defibrillation leads—suitable for insertion into a heart. One or more of these are suitable for sensing electrical signals from a portion of the heart and one or more are suitable for transmitting therapeutic doses of electrical energy. Lead system 120 also includes associated sensing and signal-conditioning electronics, such as atrial or ventricular sense amplifiers and/or analog-to-digital converters, as known or will be known in the art.

In some embodiments, lead system 150 supports ventricular epicardial rate sensing, atrial endocardial bipolar pacing and sensing, ventricular endocardial bipolar pacing and sensing, epicardial patches, and Endotak® Series and ancillary leads. In some embodiments, lead system 120 also supports two or more pacing regimens, including DDD pacing. Also, some embodiments use a housing for device 100 as an optional defibrillation electrode. The invention, however, is not limited in terms of lead or electrode types, lead or electrode configurations, sensing electronics, or signal-conditioning electronics.

Therapy system 160 includes one or more capacitors and other circuitry (not shown) for delivering or transmitting electrical energy in measured doses through lead system 150 to a heart or other living tissue (not shown). In the exemplary embodiment, therapy system 160 includes aluminum electrolytic or polymer-based capacitors. However, other embodiments use one or more other devices for administering non-electrical therapeutic agents, such as pharmaceuticals, to a heart. Thus, the invention is not limited to any particular type of therapy system.

In general operation, lead system 150 senses atrial or ventricular electrical activity and provides data representative of this activity to monitoring system 140. Monitoring system 140, specifically processor 142, processes this data according to instructions of software module 144a of memory 144. If appropriate, processor 142 then directs or causes therapy system 160 to deliver one or more measured doses of electrical energy or other therapeutic agents through lead system 150 to a heart.

More precisely, FIG. 2 shows a flow chart 200, illustrating an exemplary method at least partly embodied within software modules 144a and executed by processor 142. Flow chart 200 includes blocks 202–224, which are executed serially in the exemplary embodiment. However, other embodiments of the invention may execute two or more blocks in parallel using multiple processors or a single processor organized as two or more virtual machines or subprocessors. Moreover, still other embodiments implement the blocks as two or more specific interconnected hardware modules with related control and data signals communicated between and through the modules. Thus, the exemplary process flow is instructive to software, hardware, and firmware implementations.

In process block 202, device 120 is programmed using device programmer 110. In the exemplary embodiment, this entails wireless transceiver 130 receiving one or more cross-chamber blanking settings via wireless transceiver 118 of device programmer 110. The one or more settings take any desired value or form, for example, one or more time values ranging from 30–200 milliseconds or one or more temporal indices which are used as a basis for determining time values. In any event, upon receipt of the one or more settings, processor 142 stores them in portion 144b of memory 144. At completion of this and any other programming procedures related to operational criteria for device 120, execution of the exemplary method proceeds to block 220.

In block 220, which assumes normal post-programming operation, processor 142 retrieves one or more of the programmed cross-chamber blanking settings from portion 144b of memory 144. In the exemplary embodiment, this entails retrieving one time value, for example, 45, 65, or 85 milliseconds, for use as the cross-chamber blanking period and then computing a corresponding noise window based on the difference between a preset refractory period value (also stored in memory portion 144b), such as 86 milliseconds, and the retrieved cross-chamber blanking period. In other words, the exemplary embodiment implements a refractory period having two parts, the cross-chamber blanking part and the noise window part, with the duration of the noise window contingent on the cross-chamber blanking period. However, other embodiments implement refractory periods with more or less than two parts and/or without noise windows.

After retrieving the cross-chamber blanking setting, processor 146 registers a ventricular event sensed through lead system 150, as indicated in block 222. In the exemplary embodiment, this entails recording a marker in memory 144 along with appropriate timing indicia, before proceeding to block 224. The marker can represent either a sensed ventricular signal or a ventricular pacing signal.

In block 224, processor 142 invokes cross-chamber blanking to prevent sensing of further atrial events via lead system 150 for the duration of the cross-chamber blanking period. In the exemplary embodiment, this entails electronically disabling an appropriate portion of lead system 150 for the duration of the cross-chamber blanking period. However, other embodiments ignore or discard data from the appropriate portion of lead system 150 for the duration of the blanking period. After termination of the blanking period, sensing resumes.

FIG. 3 shows an exemplary timing diagram 300 which illustrates function of the cross-chamber blanking interval. Specifically, diagram 300 includes a horizontal time axis 302, a ventricular event marker 304, and a refractory period 306 having a programmable cross-chamber-blanking portion 306a and noise-window portion 306b. Ventricular event marker 304 represents a ventricular event sensed at block 224 in FIG. 2. Refractory period 306 represents the result of retrieving a programmed cross-chamber-blanking setting from memory portion 144b, which defines where blanking period 306a ends and noise window 306b begins. This point is shown as broken line segment 306c in the Figure. Atrial sensing is blanked during blanking period 306a. Thus, apparent atrial events such as 308 are either not sensed because of atrial sensing electronics are disabled or are ignored. Events occurring within noise window 306b are assumed to be noise and are thus similarly ignored.

CONCLUSION

In furtherance of the art, the inventors have presented an implantable dual-chamber defibrillator and/or cardioverter which includes programmable cross-chamber blanking. Unlike conventional dual-chamber devices, those in accord with the present invention allow physicians or other medically trained personnel to tailor the cross-chamber blanking period to fit the needs of individual patients.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. An implantable defibrillator comprising:
   at least first and second input leads for sensing atrial and ventricular electrical signals from a heart;
   therapy means for delivering sufficient electrical energy through one or more of the leads to at least temporarily stop the heart from fibrillating; and
   monitoring means for monitoring the electrical signals through one or more of the leads and detecting fibrillation in the heart, the monitoring means comprising:
      programmable means for storing one or more cross-chamber blanking settings; and
      means for implementing a cross-chamber blanking period based on one of the settings.

2. The implantable defibrillator of claim 1, wherein the means for implementing the cross-chamber blanking period includes means for computing a noise window width based on a difference between a preset refractory period and one of the cross-chamber blanking settings.

3. A dual-chamber defibrillation or cardioversion system comprising:
   first and second leads for sensing signals from respective first and second chambers of a heart;
   monitoring means for monitoring signals sensed at the first and second leads for detecting fibrillation in the heart, the monitoring means including:
      a memory means for storing one or more cross-chamber-blanking settings; and
      cross-chamber-blanking means responsive to one of the settings for disabling sensing signals at either the first or second lead for a preset time period based on the one setting;
   therapy means, responsive to the monitoring means, for delivering sufficient electrical energy through at least one of the first and second leads to at least temporarily stop the heart from fibrillating; and
   means for changing one or more of the cross-chamber blanking settings after implantation of the defibrillator or cardioverter.

4. The system of claim 3, wherein the memory means stores a refractory period setting and wherein the cross-chamber blanking means includes means for computing a noise window width based on a difference between the preset refractory period and one of the cross-chamber blanking settings.

5. In an implantable dual-chamber defibrillation system including a defibrillator and a programming device, a method comprising:
   storing one or more cross-chamber-blanking settings in the defibrillator;
   invoking a first cross-chamber blanking period based on one of the cross-chamber-blanking settings;
   changing one or more of the cross-chamber blanking settings in the defibrillator; and
   invoking a second cross-chamber blanking period based on the changed cross-chamber-blanking settings, with the second cross-chamber blanking period having a nominal duration different from that of the first cross-chamber blanking period.

6. The method of claim 5 wherein changing one or more of the cross-chamber blanking settings comprises wirelessly transmitting one or more cross-chamber blanking settings from the programming device to the defibrillator.

7. The method of claim 5, further comprising:
   computing a first noise window duration based at least on the one cross-chamber-blanking setting; and
   invoking a first noise window period based on the first noise window duration, with the first noise window period occurring after the first cross-chamber blanking period.

* * * * *